US00PP23266P2

(12) United States Plant Patent
Yates

(10) Patent No.: US PP23,266 P2
(45) Date of Patent: Dec. 18, 2012

(54) ***BEGONIA* PLANT NAMED 'YASPRINK'**

(50) Latin Name: ***Begonia* hybrid**
Varietal Denomination: YASPRINK

(76) Inventor: Frederic C. Yates, Congleton (GB)

( * ) Notice: Subject to any disclaimer, the term of this patent is extended or adjusted under 35 U.S.C. 154(b) by 44 days.

(21) Appl. No.: 13/066,385

(22) Filed: Apr. 13, 2011

(51) Int. Cl.
*A01H 5/00* (2006.01)

(52) U.S. Cl. ..... Plt./343
(58) Field of Classification Search ..... Plt./343
See application file for complete search history.

*Primary Examiner* — Susan McCormick Ewoldt
(74) *Attorney, Agent, or Firm* — Penny J. Aguirre

(57) ABSTRACT

A new cultivar of hybrid *Begonia* named 'YASPRINK', characterized by its large single pink flowers with a high degree of forward and horizontal facing flowers and its compact well-branched habit without cane production in its first year of growth.

2 Drawing Sheets

Botanical classification: *Begonia* hybrid.
Cultivar designation: 'YASPRINK'.

RELATED APPLICATIONS

This application is co-pending with U.S. Plant Patent applications filed for cultivars derived from the same breeding program entitled *Begonia* Plant named 'YASPWHIT' (U.S. Plant Ser. No. 13/066,386), *Begonia* Plant Named 'YADEV' (U.S. Plant Pat. No. 21,852), Plant Named 'YAMINA' (U.S. Plant Pat. No. 22,462), *Begonia* Plant Named 'YAMOUR' (U.S. Plant Pat. No. 22,788), and *Begonia* Plant Named 'YASPED' (U.S. Plant Pat. No. 22,412) and related to a cultivar from the same breeding program with a U.S. Patent, *Begonia* Plant Named 'YABOS' (U.S. Plant Pat. No. 20,093).

BACKGROUND OF THE INVENTION

The present invention relates to a new and distinct cultivar of *Begonia* plant, botanically an interspecific hybrid that includes *Begonia boliviensis* hybrids in its parentage. The new cultivar is known as *Begonia* 'YASPRINK' and will be referred to hereafter by its cultivar name, 'YASPRINK'.

The new cultivar was derived from a controlled breeding program conducted by the inventor at his nursery in Congleton, Cheshire, United Kingdom. The overall purpose of the breeding program is to make selections of *Begonia* plants to produce good basket and patio plants. 'YASPRINK' was selected in the Inventor's greenhouse in 2008 as a single unique plant from amongst the seedlings derived from a cross made in 2007 between an unnamed *Begonia* plants of hybrid origin from the Inventor's breeding program as the female and male parents.

Asexual reproduction of the new cultivar was first accomplished by stem tip cuttings in Congleton, Cheshire, United Kingdom in 2008 by the Inventor. It has been determined that the characteristics of this cultivar are stable and are reproduced true to type in successive generations.

SUMMARY OF THE INVENTION

The following traits have been repeatedly observed and represent the characteristics of the new cultivar, which in combination distinguish 'YASPRINK' as a new and distinct cultivar of *Begonia*.

1. 'YASPRINK' exhibits large, single pink flowers.
2. 'YASPRINK' exhibits flowers that have a high degree of forward and horizontal facing flowers.
3. 'YASPRINK' exhibits a compact and well-branched habit without cane production in its first year of growth.

'YASPRINK' is particular unique in having the flower form of *Begonia boliviensis* combined with a habit that lacks cane production in its first year of growth and in having a more compact habit than is typical of plants of *Begonia boliviensis*. The female parent differs from 'YASPWHIT' in having white flowers, a lower degree of forward and horizontal facing flowers and in having a less compact habit with less branching. The male parent is similar to 'YASPRINK' in having pink flowers but differs from 'YASPRINK' in having a less compact and branched habit. 'YASPRINK' can be most closely compared to cultivars from the same breeding program; 'YADEV', 'YABOS', 'YASPED', and 'YAMINA', which differ from 'YASPRINK' in having flowers that are red in color, 'YABON', which differs from 'YASPRINK' in having semi-double flowers that are yellow in color and 'YASPWHIT', which differs from 'YASPRINK' in having white flowers flushed with pink. 'YAMINA' also differs from 'YASPRINK' in having much larger flowers, larger leaves, and a groundcover type plant habit and 'YADEV' also differs from 'YASPRINK' in having leaves that are dark olive green in color. 'YASPRINK' can also be compared to 'Bonfire' (U.S. Plant Pat. No. 15,108), which differs from 'YASPRINK' in often having un-branched canes in its first year of growth, in having flowers that are orange-red in color, smaller in size, and on drooping stems and in having a plant habit that has fewer basal or secondary branches.

BRIEF DESCRIPTION OF THE DRAWING

The accompanying colored photographs illustrate the overall appearance and distinct characteristics of the new *Begonia*. The photographs were taken of a plant approximately three months in age as grown in a 15-cm container under greenhouse conditions under ambient light in Liss, Hampshire, United Kingdom.

The photograph in FIG. 1 provides a side view of 'YASPRINK' in bloom.

Figure 1:
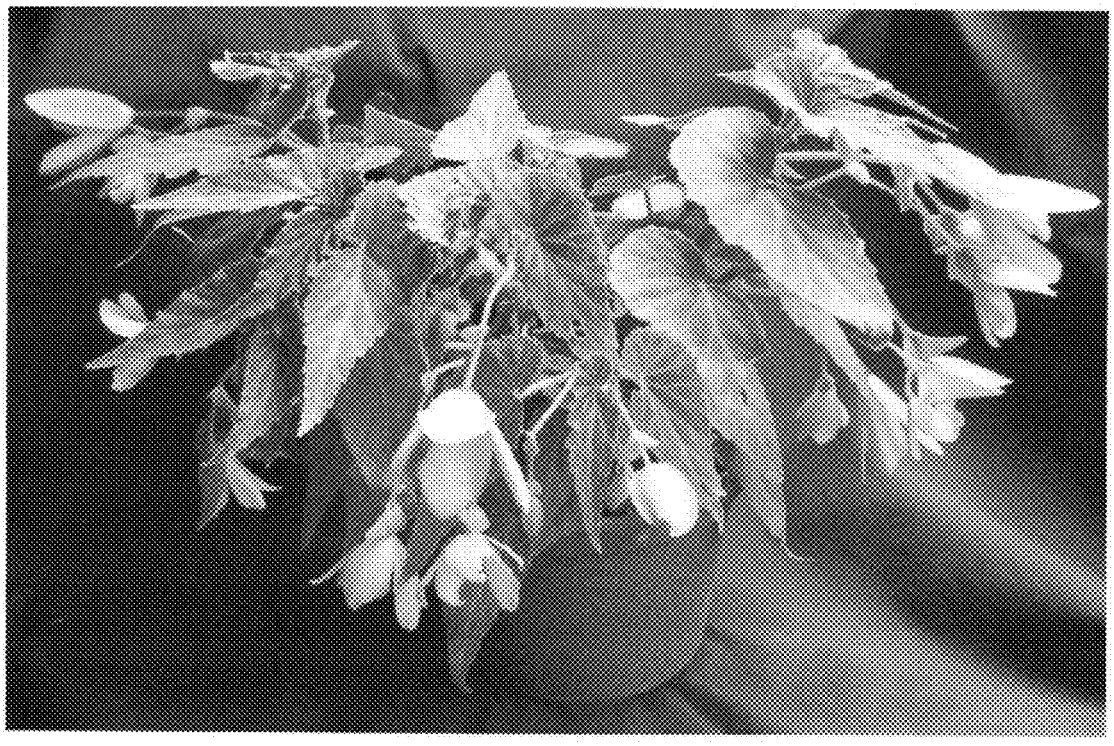
Figure 2:
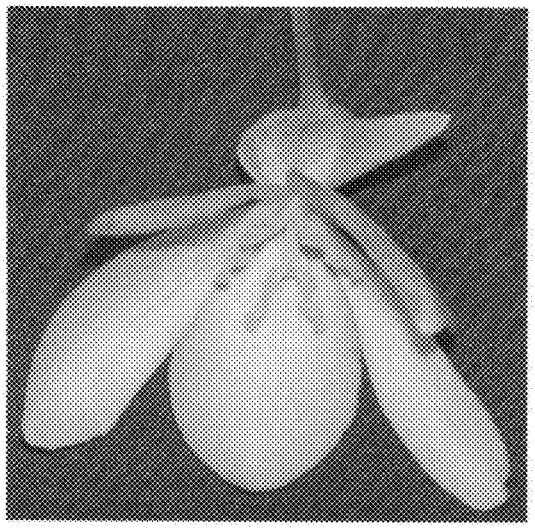

The photograph in FIG. 2 provides a close-up view of the female flowers of 'YASPRINK'.

Figure 3:
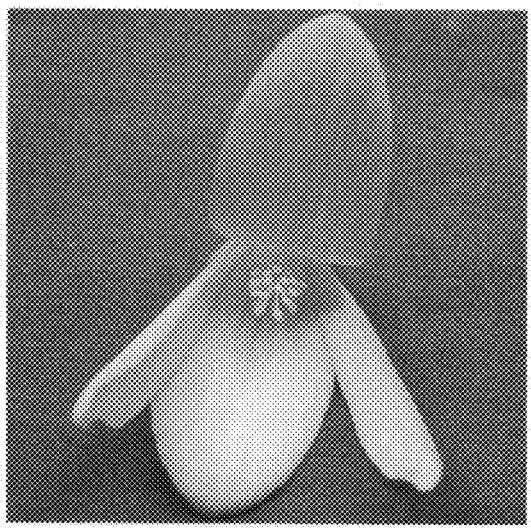

The photograph in FIG. 3 provides a close-up view of the male flowers of 'YASPRINK'.

Figure 4:
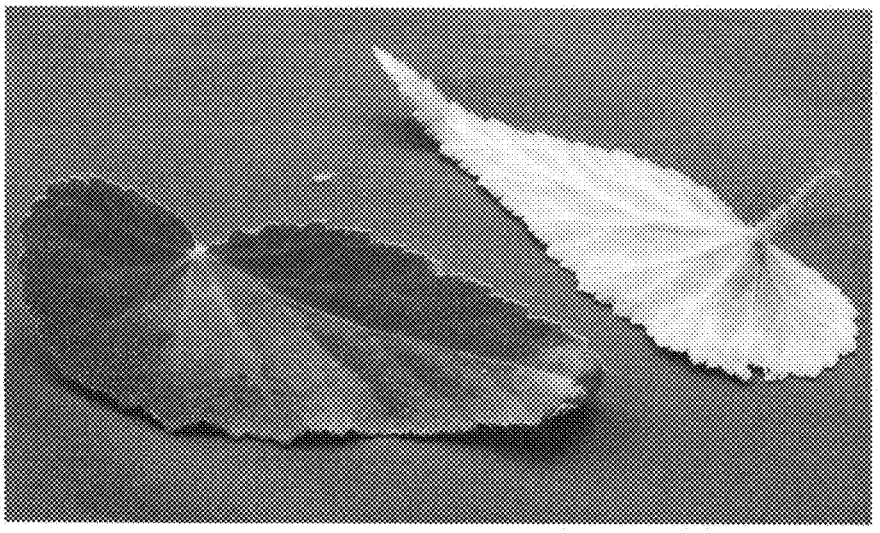

The photograph in FIG. 4 provides a close-up view of the leaves of 'YASPRINK'. The colors in the photograph may differ slightly from the color values cited in the detailed botanical description, which accurately describe the colors of the new *Begonia*.

DETAILED BOTANICAL DESCRIPTION OF THE PLANT

The following is a detailed description of plants of the new cultivar approximately three months in age as grown in 15-cm containers under greenhouse conditions with ambient light in Liss, Hampshire, United Kingdom. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General plant characteristics:

*Plant type*.—Deciduous tuberous perennial, grown primarily for use in baskets and containers.

*Plant habit*.—Spreading becoming cascading.

*Flowering period*.—From April to November.

*Height and spread*.—Reaches about 28 cm in height and about 45 cm in spread.

*Cold hardiness*.—U.S.D.A. Zone 10.

*Diseases and pests*.—No particular pests or diseases.

*Root description*.—Fleshy to fibrous.

*Tubers*.—Were not observed to be formed under typical production (April to November) for the new cultivar, this is atypical as tuber formation is typical in the first year of growth for *Begonia boliviensis* hybrids.

*Growth rate*.—Moderate.

*Propagation*.—Stem tip cuttings.

Stem description:

*Stem size*.—Average of 12.8 cm in length and 4 mm in diameter with lateral branches about 3 mm in width.

*Stem shape*.—Round, solid.

*Stem color*.—Between 200B and N199A.

*Stem surface*.—Pubescent with translucent simple hairs, lenticels absent.

*Internode length*.—Average of 2.8 cm.

*Branching habit*.—Branching from non-flowing nodes.

*Branching angle at emergence*.—About 45°.

Foliage description:

*Leaf shape*.—Strongly asymmetric, one side narrow ovate, the other side narrowly cordate and wider.

*Leaf division*.—Entire.

*Leaf base*.—Cordate.

*Leaf apex*.—Acuminate.

*Leaf venation*.—Pinnate, color; 143A on upper surface and 144C to 144D on lower surface.

*Leaf margins*.—Irregularly serrate, tips of teeth drawn out into short bristles.

*Leaf attachment*.—Petiolate.

*Leaf arrangement*.—Alternate.

*Leaf surface*.—Upper surface; few short translucent hairs, lower surface; pubescent with short simple translucent hairs.

*Leaf color*.—Upper surface N137A, lower surface 185A to 185B.

*Leaf size*.—Average of 12 cm in length and 4 cm in width.

*Leaf fragrance*.—Absent.

*Petioles*.—Between 3 and 4.8 cm in length, an average of 2 mm in width, surface is pubescent with simple translucent hairs, color; 178C, becoming slightly paler on less exposed side.

*Stipules*.—Broad triangular in shape, translucent becoming tinged with 145C in color and rapidly becoming dry and papery, about 4 mm in length and 3 mm in width.

Flower description:

*Inflorescence type*.—2 to 3 flowered cyme produced in the axils of the upper leaves, terminal male flowers developing before the 1 or 2 lateral female flowers.

*Peduncles*.—About 2 to 5 cm in length and 2 mm in width, color; N199A flushed with 179B.

*Flower persistence*.—Self-cleaning.

*Flower type*.—Single.

*Flower fragrance*.—None.

*Flower number*.—Average of 10 flowers per stem are open at one time on mature plants.

*Flower aspect*.—Mostly horizontal to hanging.

*Bracts*.—2, rounded to reniform in shape, shape of tip obtuse, about 9 mm in length and 12 mm width, color is 144C, bristly hairs at margins.

Male flowers:

*Pedicels*.—About 3.2 cm in length and 2 mm in width, color on exposed side 34A, color on shaded side 34C to 34D, glabrous surface.

*Flower buds*.—Flattened ovate in shape, about 2.9 cm in length and 16 mm in width, 39B shading to 39D in color.

*Flower size*.—About 4.4 cm in length and 4.1 cm in width.

*Tepals*.—4 in number (2 inner and 2 outer), outer tepals; ovate in shape, obtuse apex, rounded base, average of 4.2 cm in length and 2.2 cm in width, glabrous and smooth surface, entire margin, color; 48B, inner surface 48B to 48C becoming slightly paler towards the base, inner tepals; narrow ob-elliptic in shape, obtuse apex, cuneate base, average of 4.4 cm in length and 13 mm in width, glabrous and smooth surface, entire margin, color; outer surface between 48B and 50C shading to 48C, inner surface between 48B and 50C with shading towards center and base 36A to 36C.

*Stamens*.—Numerous, connate below forming a tube, about 1 cm in length and 3 mm in width, 5D in color.

*Filaments*.—About 3 mm in length and 0.5 mm in width, 5D in color.

*Anthers*.—Broadly elliptic in shape, about 1 mm in length and 1 mm in width, 14B in color.

*Pollen*.—Abundant in quantity, 10D in color.

Female flowers:

*Pedicels*.—About 3.5 cm in length and 1.5 mm in width, color on exposed side 34A, color on shaded side 34C and 34D, glabrous surface.

*Flower buds*.—Flattened ovoid in shape, about 19 mm in length and 15 mm in width, 39B shading to 39D in color.

*Flower size*.—About 3.8 cm in length and 4 cm in width.

*Tepals*.—5 in number (3 inner and 2 outer), outer tepals; ovate in shape, acute apex, rounded base, average of 3.3 cm in length and 2.8 cm in width, glabrous smooth surface, entire margin, color; 48B, inner surface 48B to 48C becoming slightly paler towards the base, inner tepals; between elliptic and narrow elliptic in shape, acute apex, cuneate base, an average of 3 to 3.5 cm in length and 11 to 14 mm in width, glabrous and smooth surface, entire margin, color; outer surface between 48B and 50C shading to 48C, inner surface between 48B and 50C with shading towards center and base 36A to 36C.

*Styles.*—3 in number, cylindrical, connate at base 1 mm, about 4 mm in length and 1 mm in width, 14A in color.

*Stigmas.*—Bifid in shape, stigmatic surfaces twisted around extensions of the style, lobes about 4 mm in length and 1 mm in width, 13B in color.

*Ovaries.*—Inferior, triangular in cross section with angles unequally winged, about 10 mm in length and 8 mm in width (excluding wings), color is 144B.

*Seed.*—Very numerous, ovoid in shape, 167A in color, extremely small in size.

It is claimed:

1. A new and distinct cultivar of *Begonia* plant named 'YASPRINK' as herein illustrated and described.

* * * * *